US011999690B2

(12) United States Patent
Sharratt et al.

(10) Patent No.: US 11,999,690 B2
(45) Date of Patent: Jun. 4, 2024

(54) METHODS FOR PREPARING PARTIALLY FLUORINATED ESTERS

(71) Applicant: Mexichem Fluor S.A. de C.V., San Luis Potosi (MX)

(72) Inventors: Andrew P. Sharratt, Runcorn (GB); John Charles McCarthy, Runcorn (GB)

(73) Assignee: Mexichem Fluor S.A. de C.V., San Luis Potosi (MX)

( * ) Notice: Subject to any disclaimer, the term of this patent is extended or adjusted under 35 U.S.C. 154(b) by 603 days.

(21) Appl. No.: 17/277,193

(22) PCT Filed: Sep. 20, 2019

(86) PCT No.: PCT/GB2019/052648
§ 371 (c)(1),
(2) Date: Mar. 17, 2021

(87) PCT Pub. No.: WO2020/058725
PCT Pub. Date: Mar. 26, 2020

(65) Prior Publication Data
US 2022/0033340 A1   Feb. 3, 2022

(30) Foreign Application Priority Data
Sep. 21, 2018 (GB) .................. 1815435

(51) Int. Cl.
*C07C 67/38* (2006.01)
*C07C 69/63* (2006.01)
(Continued)

(52) U.S. Cl.
CPC .............. *C07C 67/38* (2013.01); *C07C 69/63* (2013.01); *C07C 69/675* (2013.01);
(Continued)

(58) Field of Classification Search
CPC ... A43B 17/00; A43B 7/1455; A61B 2505/09; A61B 5/1038; A61B 5/112; A61B 5/486;
(Continued)

(56) References Cited

U.S. PATENT DOCUMENTS

| 2002/0115883 A1 | 8/2002 | Ogata et al. |
| 2003/0078352 A1 | 4/2003 | Miyazawa et al. |
| 2007/0179309 A1 | 8/2007 | Hasegawa et al. |

FOREIGN PATENT DOCUMENTS

| CN | 104536267 A | 4/2015 |
| DE | 3540378 A1 | 5/1987 |

(Continued)

OTHER PUBLICATIONS

Smith R D et al: ("The Chemistry of Carbonyl Fluoride II. Synthesis of Perfluoroisopropyl Ketones", Journal of the American Chemical Society, vol. 84, No. 22, pp. 4285-4288, Published Nov. 1, 1962) (Year: 1962).*

(Continued)

*Primary Examiner* — Yevgeny Valenrod
*Assistant Examiner* — Blaine G Doletski
(74) *Attorney, Agent, or Firm* — Crowell & Moring LLP

(57) ABSTRACT

A method for preparing a partially fluorinated ester comprising acyl and alkoxy groups wherein the acyl group comprises a branched or linear fluorine containing $C_3$-$C_8$ group with one of the structures: (Formulae (I), (II)) wherein X and Y are independently selected from: —H, —$CH_3$, —F, —Cl, —$CH_2F$, —$CF_3$—$OCF_3$, —$OCH_2CF_3$, $OCH_2CF_2CHF_2$ and —$CH_2CF_3$ (wherein both X and Y cannot be H) comprising reacting an unsaturated halocarbon: (Formula (III)) wherein A and B are independently selected from the group comprising —H, —$CH_3$, —F, —Cl, —$CH_2F$, —$CF_3$, —$OCF_3$, —$OCH_2CF_3$, $OCH_2CF_2CHF_2$ and —$CH_2CF_3$ (wherein both A and B cannot be H) with carbon monoxide and an alcohol, in the presence of a catalyst methods.

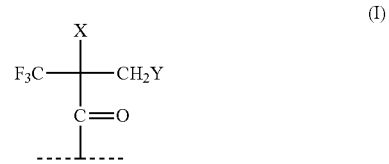

(I)

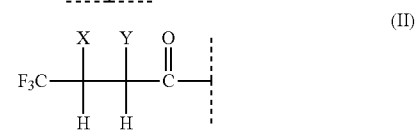

(II)

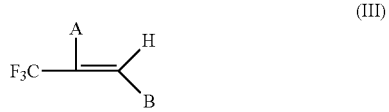

(III)

11 Claims, 11 Drawing Sheets

(51) Int. Cl.
| | |
|---|---|
| C07C 69/675 | (2006.01) |
| C07C 69/708 | (2006.01) |
| C09K 5/08 | (2006.01) |
| C10M 105/54 | (2006.01) |
| H01M 10/0569 | (2010.01) |

(52) U.S. Cl.
CPC ............. *C07C 69/708* (2013.01); *C09K 5/08* (2013.01); *C10M 105/54* (2013.01); *H01M 10/0569* (2013.01); *C10M 2211/0445* (2013.01); *H01M 2300/0034* (2013.01)

(58) Field of Classification Search
CPC ..... A61B 5/6807; A61B 5/7405; A61B 5/746; C07C 67/38; C07C 69/63; C07C 69/675; C07C 69/708; C07C 69/62; C07C 69/65; C09K 5/08; C10M 105/54; C10M 2211/0445; C10M 2207/281; C10M 2211/044; H01M 10/0569; H01M 2300/0034; H01M 2300/0028; Y02E 60/10; A61K 31/22
See application file for complete search history.

(56) References Cited

FOREIGN PATENT DOCUMENTS

| | | |
|---|---|---|
| DE | 19941696 A1 | 3/2001 |
| EP | 1637514 A | 3/2006 |
| EP | 3088380 A1 | 11/2016 |
| EP | 3275857 A1 | 1/2018 |
| JP | S63152342 A | 6/1988 |
| JP | H09157218 A | 6/1997 |
| JP | H09157326 A | 6/1997 |
| WO | WO92/12115 A1 | 7/1992 |
| WO | WO 2016/064585 A1 | 4/2016 |
| WO | WO 2017/182495 A1 | 10/2017 |
| WO | WO 2018/001232 A1 | 1/2018 |

OTHER PUBLICATIONS

Fuchikami et al. (Regioselective Hydroesterification and Hydrocarboxylation of 3,3,3-Trifluoropropene and Pentafluorostyrene Catalyzed by Phosphine-Palladium Complex, J. Org. Chem., 48, p. 3803-3807, Published 1983) (Year: 1983).*

Translation of First Office Action in corresponding Chinese Application No. 201980062046.7, dated May 7, 2023 (15 pages).

Velayutham, D., et al., "Free radical and isomerization processes during the electrochemical fluorination of n-butyryl chloride, i-butyryl chloride and pivaloyl chloride in anhydrous hydrogen fluoride," J of Flour Chem vol. 127 (2006) 1111-1118.

Scrivanti, A., et al., "Alkoxycarbonylation of 3,3,3-Trifluoropropyne: an Intriguing Reaction to Prepare Trifluoromethyl-Substituted Unsaturated Acid Derivatives," Adv. Synth. Catal. 2002, 344, No. 5, pp. 543-547.

Papp, H., and Baerns, M., "Industrial Application of CO Chemistry for the Production of Specialty Chemicals," Chap. 10, Studies in surface science and catalysis, 64, 430, 1991.

Matteoli, U., et al., "Esters and N,N-dialkylamides of 2-(trifluoromethyl)acrylic acid (TFMAA) through Pd-catalysed carbonylation of fluorinated unsaturated substrates," J. Mol. Cat. A.: Chem., vol. 143 (1999), 287-295.

Ojima, I., "New Aspects of Carbonylations Catalyzed by Transition-Metal Complexes," Chem. Rev. 1988, vol. 88, 1011-1030.

Brookes, C.J., et al., "Reactions of Fluoroalkyl Radicals Generated Electrochemically. Part 1. Additions of Trifluoromethyl Radicals to Olefinic and Acetylenic Bonds," Journal of the Chemical Society—Perkin Transactions 1, 1978, No. 9, 202-209.

Watanabe, S., et al., "Reactions of Monoesters of Ethylene Glycol with N, N-Diethyl-1,1,2,3,3,3-Hexafluoropropylamine," Journal of Fluorine Chemistry (1987) vol. 36(3), 361-372.

Schmidt, H., et al., Journal Für Praktische Chemie : Practical Applications and Applied Chemistry : Covering All Aspects of Applied Chemistry, Wiley, DE, vol. 2, No. 1-2, Jul. 1, 1955 (Jul. 1, 1955), p. 105-120.

International Search Report, and Written Opinion, in Application No. PCT/GB2019/052648, dated Mar. 27, 2020, 19 pages.

International Preliminary Report on Patentability in Application No. PCT/GB2019/052648, dated Mar. 23, 2021, 12 pages.

Search Report in UK Application No. GB 1815435.1, dated Oct. 17, 2019, two pages.

Bhadury, P.S., et al., "A semi-molten mixture of hexadecyltributylphosphonium bromide and potassium fluoride in the synthesis of organofluorine compounds," *Journal of Luorine Chemistry*, Elsevier, NL, vol. 99, No. 2, Nov. 1, 1999, pp. 115-117.

Bredenkamp, Tyler, et al., "The Pd-catalysed hydromethoxycarbonylation of aliphatic internal alkenes with minimal double bond isomerisation," *Catalysis Communications*, vol. 96, Jun. 1, 2017, pp. 74-78.

Buxton, W., et al., "Studies upon alpha-trifluoromethylacrylic acid, alpha-trifluoromethylpropionic acid, and some derived compounds," *Journal of the Chemical Society*, Jan. 1, 1954, pp. 366-384.

Database Registry, (online) Chemical Abstracts Service, Columbus Ohio, Jun. 16, 2011, retrieved from STN Database accession No. 1309602-63-8 abstract.

Database Registry, (online) Chemical Abstracts Service, Columbus, Ohio, Aug. 14, 2017, retrieved from STN Database accession No. 2113454-77-4 abstract.

International Search Report for corresponding International patent application No. PCT/GB2019/052648, dated Mar. 20, 2020.

Pervova, M.G., et al., "Synthesis and GC-MS Study of Fluorinated Esters Derived from Thrimethylolpropane," *Russian Journal of General Chemistry*, vol. 78, No. 9, Sep. 1, 2008, pp. 1701-1706.

Renaud, R.N., et al., "Electrochemical Oxidation of Trifluoroacetic Acid in an Organic Substrate. III. In the Presence of Substituted Malonic Acid Half Esters and Unsaturated Carboxylic Acid Esters," *Canadian Journal of Chemistry*, NRC Research Press, CA, vol. 53, Jan. 1, 1975, pp. 529-534.

Smith, R.D., et al., "The Chemistry of Carbonyl Fluoride II. Synthesis of Perfluoroisopropyl Keytones," *Journal of the American Chemical Society*, vol. 84, No. 22, Nov. 1, 1962, pp. 4285-4288.

Written Opinion of the International Search Authority for corresponding International patent application No. PCT/GB2019/052648, dated Mar. 20, 2020.

* cited by examiner

METHODS FOR PREPARING PARTIALLY FLUORINATED ESTERS

CROSS-REFERENCE TO RELATED APPLICATIONS

This application is the U.S. National Stage application of PCT International application no. PCT/GB2019/052648, filed on Sep. 20, 2019, titled METHODS, designating the United States, which claims priority to Great Britain application no. 1815435.1 filed on Sep. 21, 2018, the contents of which are each incorporated herein by reference in their entirety.

The present invention relates to methods of preparing partially fluorinated esters comprising acyl and alkoxy groups.

Partially fluorinated esters are an important class of materials with significant commercial value. They are commonly used without modification as synthetic intermediates and as solvents in electronic devices such as batteries (e.g. lithium batteries) and to manufacture products such as lubricants, sealants, and coatings.

The production of esters is known in the art. One such method involves the catalytically driven alkoxycarbonylation of alkenes with carbon monoxide and an alcohol. This is described in, for example, H. Papp and M. Baerns, Studies in surface science and catalysis, 64, 430, 1991.

This method has been extended to certain haloalkenes. The carbonylation of 2-bromo-3,3,3-trifluoropropene has been reported in J. Mol. Cat. A.: Chem., 143, 287-295, 1999. The carbonylation of 2-bromo-3,3,3-trifluoropropene has also been reported in Chem. Revs, 88, 1011-1030, 1988.

The listing or discussion of a prior-published document in this specification should not necessarily be taken as an acknowledgement that the document is part of the state of the art or is common general knowledge.

To date the esterification of alkenyl fluorides/alkenes with multiple $CF_3$ groups and/or $CF_3$ and fluorine substituents on the alkene double bond, for example 2,3,3,3-Tetrafluoropropene (1234yf), 1,3,3,3-Tetrafluoropropene (1234ze) and from fluorobutenes, such as 1,1,1,4,4,4-hexafluoro-2-butene (1336mzz) and hexafluoroisobutylene (HFIB), has not been reported but is desirable because of the utility such products might find in a wide variety of applications such as synthetic intermediates, solvents, lubricants, sealants and coatings.

Methods of the Invention

According to a first aspect of the invention there is provided a method for preparing a partially fluorinated ester comprising acyl and alkoxy groups wherein the acyl group comprises a branched or linear fluorine containing $C_3$-$C_6$ group with one of the structures:

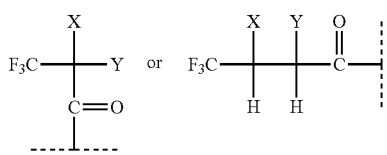

wherein X and Y are independently selected from:
—H, —$CH_3$, —F, —Cl, $CH_2F$, $CF_3$, —$OCF_3$, —$OCH_2CF_3$, $OCH_2CF_2CHF_2$ and —$CH_2CF_3$ (wherein both X and Y cannot be H)

comprising reacting an unsaturated halocarbon:

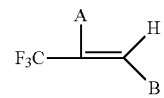

wherein A and B are independently selected from the group comprising —H, —$CH_3$, —F, —Cl, —$CH_2F$, —$CF_3$, —$OCF_3$, —$OCH_2CF_3$·$OCH_2CF_2CHF_2$ and —$CH_2CF_3$ (wherein both A and B cannot be H) with carbon monoxide and an alcohol, in the presence of a catalyst.

Preferably the acyl function contains from 3 to 7 carbon atoms, most preferably 4 to 5 carbon atoms.

Preferably the unsaturated halocarbon contains from 3 to 6 carbon atoms, more preferably 3 to 5 carbon atoms and most preferably 3 to 4 carbon atoms.

In a preferred embodiment the partially fluorinated ester comprises one of the group comprising

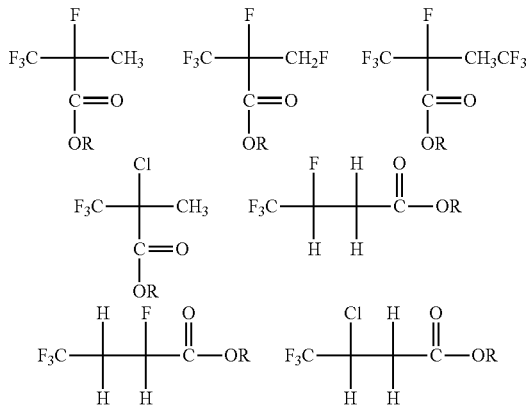

The method may comprise reacting 2,3,3,3-Tetrafluoropropene (1234yf) and/or 2-chloro-3,3,3-trifluoropropene (1233xf) with carbon monoxide and an alcohol to form $CF_3CF(CH_3)CO_2R$ and/or $CF_3CHFCH_2CO_2R$ or $CF_3CCl(CH_3)CO_2R$ and/or $CF_3CHClCH_2CO_2R$.

The method may comprise reacting 1,3,3,3-Tetrafluoropropene (1234ze) with carbon monoxide and an alcohol to form $CF_3CH(CH_2F)CO_2R$ and/or $CF_3CH_2CHFCO_2R$.

The method may comprise reacting 1,1,1,4,4,4-hexafluoro-2-butene (1336mzz) with carbon monoxide and an alcohol to form $CF_3CH_2CH(CF_3)CO_2R$.

The method may comprise reacting 1 3,3,3-trifluoro-1(2,2,2-trifluoroethoxy)prop-1-ene with carbon monoxide and an alcohol to form $CF_3CH(CO_2R)CH_2OCH_2CF_3$ or $CF_3CH_2CH(O\ CH_2CF_3)CO_2R$.

R is an alkoxy or an alkyl group, with the formula $OC_nH_{2n+1-x}F_x$ or $C_nH_{2n+1-x}F_x$ respectively.

R is derived from a branched or linear monohydric alcohol with the formula $HOC_nH_{2n+1-x}F_x$.

Preferably in $HOC_nH_{2n+1-x}F_x$, n is from 1 to about 10, more preferably n is from 1 to about 7, more preferably n is from 1 to about 5, most preferably n is from 1 to about 3.

Preferably in $HOC_nH_{2n+-x}F_x$, x has a value from 0 to $2n+1$. For the most preferred values of n, x is preferably 0, 3 or 4.

Most preferably R is methyl, ethyl or trifluorethyl. The alcohol is preferably one or more of methanol, ethanol or trifluoroethanol.

Without wishing to be bound by theory in the process it is postulated that the alkene bonds to the catalyst. This is believed to occur via the π-orbitals of the alkene double bond. In this regard, given the electron withdrawing effect of the fluorine containing substituents around the alkene double bond it has been found to be surprising that the fluorinated alkenes of the present invention are still able to bond to the catalyst. In other words, it has been found to be surprising that the presence of the fluorine containing substituents around the alkene bond does not restrict/lower the extent of the π-orbitals of the alkene double bond interacting with the catalyst such that bonding to the catalyst is prevented/hindered.

In the method of the invention the resultant ester may comprise more than one isomer. Without wishing to be bound by theory it is thought that the reaction regioselectivity is influenced by one or more factors which include steric hindrance, intermediate stabilisation, kinetic or thermodynamic factors. One or more of these factors may influence the product distribution. For certain partially fluorinated $C_3$-$C_7$ alkenes the influence of one of the factors may be such that only one isomer is produced, which is especially desirable.

However, where mixtures of products are formed they can be separated if desired by any means known in the art such as for example distillation. It will be appreciated though that in some cases separation may be difficult because of the similarity in properties of the products and because associations between them e.g. azeotropes may make separation impossible. As a result, this patent also includes compositions comprising mixtures, including azeotropic compositions, of isomers prepared by the processes described and any separations techniques applied to them.

For the avoidance of doubt, it is to be understood that where a compound may exist as one of two configurational isomers, e.g. E and Z isomers around a double bond, the use of the term without an isomer designation (e.g. R-1234ze) is to refer to either isomer or a mixture of isomers.

The method of the first aspect of the invention is illustrated in Reaction Scheme (I);

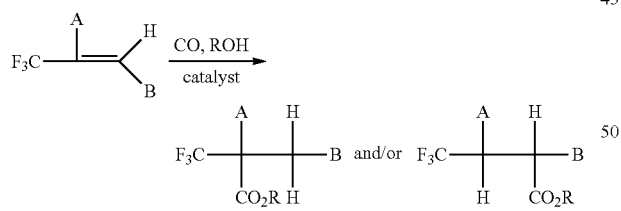

wherein A, B and R are as described above.
The 5 most preferred options for the groups as below:—
i) Preferably A is H and B is F.
ii) Preferably A is F and B is H.
iii) Preferably A is H and B is $CF_3$.
iv) Preferably A is $CF_3$ and B is H.
v) Preferably A is is H and B is $OCH_2CF_3$.

Optionally the catalyst comprises a group 8-12 metallic component (such as iron, ruthenium, osmium, cobalt rhodium, iridium, nickel, palladium platinum, copper, silver, gold, zinc, cadmium, mercury), comprising a halogen ligand (such as fluorine, chlorine, bromine, iodine) and a phosphorous containing ligand $PR_3$ where R=H, Ph, alkyl etc.

A preferred catalyst comprises $Cl_2Pd(PPh_3)_2$. A further preferred catalyst comprises bis(dicyclohexyl)(4-dimethylaminophenylphosphine) palladium (II) chloride.

Optionally the catalyst comprises a group 8-12 metallic compound (such as iron, ruthenium, osmium, cobalt rhodium, iridium, nickel, palladium platinum, copper, silver, gold, zinc, cadmium, mercury), comprising a carbonyl ligand and optionally another ligand (such as halogen, alkyl, phosphorous containing ligand).

Preferred catalysts include $Fe(CO)_5$, $CO_2(CO)_8$, and/or $Ru_3(CO)_{12}$.

The method is preferably performed in the liquid phase in a solvent. Any suitable solvent may be used, preferred solvents include toluene, THF, and acetonitrile. An alcohol can also be used as a solvent. In this regard the alcohol used for the solvent would ideally be the same as the alcohol used in the reaction. Most preferably the solvent is free of water to avoid the formation of carboxylic acids. If water is present, either as an impurity or as an additive, then free carboxylic acids will be formed with similar structures to the esters described above.

The method is typically conducted in the liquid phase at elevated temperature. A temperature of from about 60 to about 140° C. may be used, e.g. from about 100° C. to about 120° C., such as about 100° C. Lower and higher temperatures can be used. Typically, lower or higher temperatures are used to achieve a desirable rate of reaction, regioselectivity or if the reaction pressure is more elevated or less elevated, respectively.

Preferably the method is performed at a pressure of from about 10 to about 150 bara, more preferably from about 20 to about 140 bara, more preferably from about 30 to about 130 bara, more preferably from about 40 to about 120 bara, more preferably from about 40 to about 110 bara and most preferably about 40 to about 100 bara. Typically, lower or higher pressures are used if the reaction temperature is raised or lowered, respectively.

In the present invention, the method may be carried out batch-wise or continuously. Any suitable apparatus may be used, such as a static mixer, a tubular reactor, a stirred tank reactor or a stirred vapour-liquid disengagement vessel.

The products of the reaction maybe recovered by any suitable means for example phase separation, extraction, distillation etc.

Compounds & Compositions of the Invention

According to a second aspect of the invention there is provided a compound which is

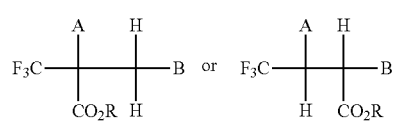

in which wherein A, B are R are as defined above.
There are 6 most preferred options for the groups as below:—
i) Preferably A is H and B is F.
ii) Preferably A is F and B is H.
iii) Preferably A is H and B is $CF_3$.
iv) Preferably A is $CF_3$ and B is H.
v) Preferably A is Cl and B is H.
vi) Preferably A is H and B is $OCH_2CF_3$.

Most preferably R is methyl, ethyl or trifluorethyl.

The compounds of the second aspect of the invention may be used in the preparation of an unsaturated ester. Preferably the ester is unsaturated in the acyl group. Preferably the alkene bond of the ester is conjugated with carbonyl bond of the ester. Most preferably the ester is (trifluorometh)acrylate:

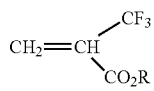

(wherein R is as defined above).

The compounds of the second aspect of the invention may be transformed into an unsaturated ester (most preferably (trifluorometh)acrylate) by any suitable method. Preferred methods comprise elimination of HX (HCl or HF) by treatment with a metal hydroxide or other suitable base.

The compounds of the second aspect of the invention may be used as a synthetic intermediate.

The compounds of the second aspect of the invention may be also used as a battery solvent component (e.g. in a lithium battery). Here the compounds are found to be beneficial as a result of their physical properties, electrochemical stability, compatibility with battery electrodes and low flammability.

The compounds of the second aspect of the invention may be used in the preparation of a polyol ester. This is preferably achieved in a reaction in which the alkoxy group is substituted for an alternative alkoxy group from a polyol.

Such polyol esters have been found to be excellent lubricants in compositions comprising lubricants and refrigerants in heat transfer applications, such as in heating, refrigeration and air conditioning systems. Such lubricants are included in heat transfer compositions to ensure continued smooth operation of the systems mechanical components.

It is necessary that lubricants used in heat transfer compositions are compatible with the refrigerants in the compositions. The compatibility of the lubricant and the refrigerant is predicated on a number of factors, such as a desire for at least partial miscibility at part of the operating temperature range, a low tendency to degrade or react in use, appropriate viscosities for the application and a balance of physical properties of refrigerant/lubricant mixtures such that oil which migrates from the compressor can be transported round the system and back to the compressor.

There is, therefore, a need for lubricants that can be used in conjunction with heat transfer fluids, both those currently used and those proposed as replacement compositions. In particular, lubricants are desired that are miscible with a wide range of heat transfer fluids, possess an appropriate viscosity, do not reduce the performance of heat transfer fluids and have low flammability; all in addition to successfully functioning as a lubricant.

Lubricants with low flammability are particularly important for heat transfer fluids that are used in automobile air-conditioning with flammable refrigerants such as 1234yf, 1234ze and blends comprising them, as such compositions are in danger of coming into contact with hot metal surfaces of the engine.

These polyol esters have been found to address the issues outlined above.

The ester may be transformed into a polyol ester by any suitable method. One preferred method comprises indirect transformation through one or more intermediates such as conversion of the ester to, for example, an acid, acid chloride or acid anhydride and processing of the intermediate to the polyol ester. Another preferred method comprises direct transformation of ester through transesterification. In the transesterification reaction the R group is substituted for an alternative R group (for example from a polyol). It is possible that a number of different esters may be produced. These esters may be separated (such as by distillation) or used as an admixture.

In the reaction of the ester with a polyol it will be appreciated that the reaction may not proceed to completeness. It is expected that a portion of the hydroxyl groups of the polyol may be esterified in the transesterification reaction. To achieve complete esterification the reaction mixture exiting the reactor may be recycled back into the reactor/into a second reactor, so that more of the (non-esterified) hydroxyl groups of the polyol will be esterified.

Alternatively/additionally in a preferred embodiment partial esterification of the polyol with a compound of the second aspect of the invention may be encouraged.

The partially esterified polyol with or without an amount of the initial polyol and/or initial ester may be separated or produced as a final admixture for use (e.g. as a lubricant in a heat transfer composition).

Alternatively/additionally in another preferred embodiment partial esterification of the polyol with a compound of the second aspect of the invention may be encouraged, wherein one or more of the remaining OH group(s) on the polyol are esterified with a fatty carboxylic acid. Preferably the fatty carboxylic acid has from 6 to 15 carbon atoms. As will be understood fatty acids often come from natural sources, as such this term "fatty carboxylic acid" will be understood to comprise a mixture of linear or branched, saturated and non-saturated fatty carboxylic acids.

Such esterified polyols with or without an amount of the initial polyol and/or initial ester may be separated or produced as a final admixture for use (e.g. as a lubricant in a heat transfer composition).

A combination blend comprising an admixture of differently esterified polyols may be produced as a final admixture for use (e.g. as a lubricant in a heat transfer composition). One such combination may comprise a first polyol, which is at least partially (and optionally fully) esterified by esterification with a compound of the second aspect of the invention, in combination with a second polyol which is at least partially (and optionally fully) esterified by esterification with a non-fluorinated fatty carboxylic acid. A second such combination may comprise a first polyol, which is at least partially esterified by esterification with a compound of the second aspect of the invention and at least partially esterified by esterification with a non-fluorinated fatty carboxylic acid, in combination with a second polyol which is at least partially (and optionally fully) esterified by esterification with a non-fluorinated fatty carboxylic acid.

The first and second polyol (before esterification) may be the same or may be different.

In a yet a further aspect of the invention it is preferred that the polyol ester is produced directly in the alkoxycarbonylation reaction.

Thus, according to a third aspect of the invention there is provided method for preparing a partially fluorinated ester of the Formula (II);

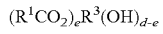

wherein $R^1$ comprises a branched or linear fluorine containing $C_3$-$C_7$ group with one of the structures:

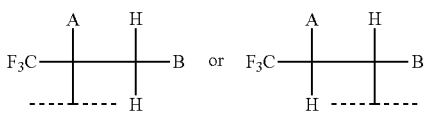

wherein A and B are as described above
comprising reacting an unsaturated halocarbon, as previously defined,
with carbon monoxide and a polyhydric alcohol $R^3(OH)_d$, in the presence of a catalyst,
wherein d is from 2 to 5, e is from 2 to 5 and wherein $R^3$ comprises a $C_2$ to $C_7$ group, preferably alkyl.

Preferably $R^3$ comprises a branched $C_2$ to $C_7$ alkyl group. $R^3$ may be fluorinated or otherwise substituted. This substitution may be present or introduced on the polyhydric alcohol before and/or after formation of $(R^1CO_2)_e R^3(OH)_{d-e}$.

Alternatively, $R^1$ may partially comprises a branched or linear fluorine containing $C_3$-$C_7$ group as above and may further partially comprise a branched or linear alkyl/alkenyl group. This could be the case wherein the unsaturated halocarbon comprises an alkene/alkyne. Preferred alkenes/alkynes include $C_2$ to Cao alkenes/alkynes.

More preferably d is from 2 to 4, for example 2 or 3.

Clearly d and e are interrelated. It will be appreciated that e cannot be greater than d; e may equal d.

It is preferred that $(R^1CO_2)_e R^3(OH)_{d-e}$ has no residual OH groups. Preferably d−e=0.

It is possible that a portion of the $R^3(OH)_d$ may have some residual OH groups. These species may be removed from the admixture (such as by distillation) and/or treated (such as by recycling into the akoxylcarbonylation reaction). In the cases where e is less than d the partially fluorinated ester of the Formula (II) may be further esterified, e.g. by reaction with a fatty carboxylic acid having from 6 to 15 carbon atoms.

Preferred polyols include ethylene glycol, glycerol, neopentyl glycol (2,2-dimethyl propane diol), 1,2,3-trimethylol propane and pentaerythritol.

The use of effective amounts of compounds according to Formula (II) in a lubricant composition or a heat transfer composition is advantageous due to their thermal and mechanical stability, lubricity, viscosity, pour point, anti-oxidation and anti-corrosive properties.

In an embodiment, the compositions of the invention may have improved heat transfer properties than the heat transfer fluid alone.

Without wishing to be bound by theory, it is believed that compounds of Formula (II) may further act as heat transfer agents and therefore increase the heat transfer properties of the compositions of the invention.

The invention also provides a heat transfer device containing a composition of the invention and/or the use of a composition of the invention in a heat transfer device.

Conveniently, the heat transfer device may be a refrigeration device.

Advantageously, the heat transfer device may be selected from the group consisting of automotive air conditioning systems, residential air conditioning systems, commercial air conditioning systems, residential refrigerator systems, residential freezer systems, commercial refrigerator systems, commercial freezer systems, chiller air conditioning systems, chiller refrigeration systems, and commercial or residential heat pump systems.

Conveniently, the compound according to Formula (II), when formulated as lubricant composition, may be comprised within a lubricant composition in a proportion of at least 10 to 100 wt %, preferably in a proportion of 10 to 90 wt %, preferably in a proportion of 10 to 75 wt %, such as 10, 20, 30, 40 or 50 wt % of the lubricant composition.

Advantageously, compounds according to Formula (II) may be miscible with existing polyalkylene glycol, polyalkylene glycol ester, polyol ester or polyvinyl ether lubricating oils.

Preferably, compounds according to Formula (II) may be at least partially miscible with perfluorinated polyether (PFPE) lubricating oils.

Advantageously, the lubricant composition may further comprise a stabiliser. Conveniently, the stabiliser may be selected from diene-based compounds, phosphates, phenol compounds and epoxides, and mixtures thereof.

Preferably, the lubricant composition further may comprise an additional flame retardant. Advantageously, the flame retardant may be selected from the group consisting of tri-(2-chloroethyl)-phosphate, (chloropropyl) phosphate, tri-(2,3-dibromopropyl)-phosphate, tri-(1,3-dichloropropyl)-phosphate, diammonium phosphate, various halogenated aromatic compounds, antimony oxide, aluminium trihydrate, polyvinyl chloride, a fluorinated iodocarbon, a fluorinated bromocarbon, trifluoro iodomethane, perfluoroalkyl amines, bromo-fluoroalkyl amines and mixtures thereof.

Conveniently, the Global Warming Potential (GWP) of the compositions of the invention may be less than about 3500, 3000, 2500 or 2000. For instance, the GWP may be less than 2500, 2400, 2300, 2200, 2100, 2000, 1900, 1800, 1700, 1600 or 1500. The GWP of the compositions of the invention preferably is less than 1400, 1300, 1200, 1100, 1000, 900, 800, 700, 600 or 500. Particularly preferred compositions will have a GWP much less than 100, for example between 0 and 10.

Preferably, the compounds of the invention may have zero or near zero ozone depletion.

The invention will now be illustrated with reference to the following non-limiting examples.

EXAMPLES

Example 1A—Esterification of HFO with Alcohol Using Bis(Triphenylphoshine)Palladium (II) Chloride Catalyst The following steps were followed.

The reactor was charged with catalyst (bis(triphenylphoshine)palladium (II) chloride), solvent and alcohol, inside a nitrogen purged glovebox. Then sealed and removed from the glovebox.

The HFO substrate was then added from a pre-loaded and weighed sample bomb.

The reactor was then pressurised with CO to c.a. 37 barg and the reactor contents heated to the desired reaction temperature with stirring.

At the end of the experiment the reactor contents were cooled, and any residual pressure vented before the crude product was recovered.

The recovered crude product was analysed by GC-MS and NMR spectroscopy.

| Expt. | EM1** | EM2 | EM8 | EM5 | EM3 | EM7 | EM4 |
|---|---|---|---|---|---|---|---|
| HFO (g) | 1243zf 9 | 1234ze-E 7.4 | 1234ze-E 10.8 | 1234ze-E 3 | 1234ze-Z 10.1 | 1336mzz-E 5.5 | 1336mzz-Z 5 |
| Catalyst (g) | 0.38 | 0.31 | 0.3 | 0.13 | 0.33 | 0.31 | 0.31 |
| Solvent (g) | ACN 20.41 | ACN 22.4 | ACN 29.16 | ACN 15.74 | ACN 23.05 | ACN 28.86 | ACN 22.85 |
| Alcohol (g) | EtOH 6.73 | EtOH 7.06 | EtOH 8.91 | EtOH 4.5 | EtOH 8.15 | EtOH 9.76 | EtOH 8.9 |
| Temperature (° C.) | 100 | 100 | 100 | 100 | 110 | 100 | 100 |
| Pressure (barg) | 47.8 | 46.4 | 46.4 | 49.4 | 45 | 47 | 46.2 |
| Pressure drop (barg) | 29.2 | 4.8 | 7 | 1.6 | 4.4 | 2 | 5.8 |
| Duration (hrs) | 50 | 71 | 70.5 | 73 | 50 | 47 | 71 |
| Ester yield (%) | ND | ND | 33.7 | 36.8 | 51.6 | 41.3 | 100 |
| Regioselectivity n-:iso- | 1:0.7 | | 100% n-isomer | | | Only 1 isomer possible | |

| Expt. | EM6 | EM9 | EM10 | EM11 | EM12 | EM13 | EM14 | EM15 |
|---|---|---|---|---|---|---|---|---|
| HFO (g) | 1234yf 5.2 | 1234yf 10.6 | 1234yf 8.8 | 1234yf 10.1 | 1234yf 10.5 | 1234yf 11.2 | 1234yf 10.7 | 1233xf 9.0 |
| Catalyst (g) | 0.3 | 0.6 | 0.27 | 0.58 | 0.62 | 0.6 | 0.6 | 0.58 |
| Solvent (g) | ACN 25 | ACN 29.71 | ACN 28.77 | ACN 28.8 | ACN 28.6 | Toluene 29.7 | THF 29.1 | ACN 29.7 |
| Alcohol (g) | EtOH 10.71 | EtOH 9.66 | EtOH 8.9 | EtOH 9.3 | MeOH 10.5 | EtOH 9.3 | EtOH 9.3 | EtOH 9.4 |
| Temperature (° C.) | 100 | 100 | 120 | 120 | 120 | 120 | 120 | 120 |
| Pressure (berg) | 44.4 | 48.4 | 51.2 | 52.6 | 49.2 | 55.2 | 50 | 51 |
| Pressure drop (berg) | 5.6 | 17.2 | 13.6 | 23 | 9 | 31.8 | 26 | 3.5 |
| Duration (hrs) | 66 | 72 | 70 | 92 | 46 | 48 | 73 | 71 |
| Ester yield (%) | 100 | 72.4 | 73.2 | 91.7 | 48.9 | 56.2 | ND | 26.3 |
| Regioselectivity n-:iso- | | | | 1:100 | | | | 1:10.8 |

**comparative example.

Example 1B—Esterification of 1234yf with Ethanol in Acetonitrile Using Bis(Di-(Tert Butyl)(4-Trifluoromethyl)Phenyl(Phosphine) Palladium (II) Chloride or Bis(Dicyclohexyl)(4-Dimethylaminophenylphosphine) Palladium (II) Chloride Catalyst The same basic procedure as example 1A was used. The catalyst was selected from bis(di-(tert butyl)(4-trifluoromethyl)phenyl(phosphine) palladium (II) chloride (A) or bis(dicyclohexyl)(4-dimethylaminophenylphosphine) palladium (II) chloride (B)

| Catalyst (g) | 1234yf (g) | Ethanol (g) | Time (hrs) | Temperature (° C.) | CO (Barg) | Pressure drop (Barg) | Yield (%) | n:i |
|---|---|---|---|---|---|---|---|---|
| A (0.50) | 10.5 | 9.35 | 66 | 120 | 47.5 | 28.5 | 99.4 | 1:1.49 |
| B (0.52) | 11.2 | 9.49 | 46 | 120 | 54 | 8 | 33.5 | 1:5.8 |

Example 2—Esterification of HFO with Alcohol

The same basic procedure as example 1A was used. The experiments were repeated in a larger scale reactor (450 ml).

| Expt. | Parr1 ** | Parr2 | Parr3 | Parr4 |
|---|---|---|---|---|
| HFO (g) | 1243ze-E 39.2 | E-1234ze-E 36.9 | 1234yf 35.1 | 1234yf 36 |
| Catalyst (g) | A 1.27 | B 1.3 | B 1.26 | B 1.2 |// -continued
| Expt. | Parr1 ** | Parr2 | Parr3 | Parr4 |
| Solvent (g) | ACN 133.1 | ACN 131.1 | ACN 127.66 | ACN 137 |
| Alcohol (g) | EtOH 34.5 | EtOH 34.3 | EtOH 37.86 | EtOH 35 |
| Temperature (° C.) | 100 | 100 | 100 | 100 |
| Pressure (barg) | 78 | 80 | 79 | 102* |

-continued

| Expt. | Parr1 ** | Parr2 | Parr3 | Parr4 |
|---|---|---|---|---|
| Pressure drop (barg) | 6 | 6 | 11 | 20 |
| Duration (hrs) | 72 | 72 | 69 | 72 |
| Ester yield (%) | 24.6 | 25.0 | 89.6 | 94.4 |

*80 bar CO and 22 bar nitrogen.
** comparative example.

Example 3—Esterification of 1243zf with Diol

The following steps were followed.
The reactor was charged with catalyst (bis(triphenylphoshine)palladium (II) chloride (2.26 g)), solvent (acetonitrile, 133 g) and alcohol (2,2-dimethyl propane diol, 36.4 g), inside a nitrogen purged glovebox. Then sealed and removed from the glovebox.
The reactor contents were stirred.
The HFO substrate (1243zf, 39 g) was then added from a pre-loaded and weighed sample bomb.
The reactor was then pressurised with CO to c.a. 110 barg and the reactor contents heated to the desired reaction temperature (120° C.) with stirring.
After 22 hours the pressure had dropped to 62 barg.
The reactor contents were cooled and any residual pressure vented.
A second portion of HFO substrate (1243zf, 43 g) was then added from a pre-loaded and weighed sample bomb.
The reactor was then pressurised with CO to c.a. 108 barg and the reactor contents heated to the desired reaction temperature (120° C.) with stirring.
After 72 hours the pressure had dropped to 80 barg.
At the end of the experiment the reactor contents were cooled, and any residual pressure vented before the crude product was recovered.
The recovered crude product was analysed by GC-MS and NMR spectroscopy. GC-MS analysis of the crude reaction mixture showed that the reaction mixture comprised all 5 possible ester products:

| Product | GC-MS Area % |
|---|---|
| $H_3C-\overset{CH_2OCOCH(CH_3)CF_3}{\underset{CH_2OH}{\overset{|}{C}}}-CH_3$ | 12.6 |
| $H_3C-\overset{CH_2OCOCH_2CH_2CF_3}{\underset{CH_2OH}{\overset{|}{C}}}-CH_3$ | 7.2 |
| $H_3C-\overset{CH_2OCOCH(CH_3)CF_3}{\underset{CH_2OCOCH(CH_3)CF_3}{\overset{|}{C}}}-CH_3$ | 20.4 |
| $H_3C-\overset{CH_2OCOCH_2CH_2CF_3}{\underset{CH_2OCOCH(CH_3)CF_3}{\overset{|}{C}}}-CH_3$ | 40.6 |
| $H_3C-\overset{CH_2OCOCH_2CH_2CF_3}{\underset{CH_2OCOCH_2CH_2CF_3}{\overset{|}{C}}}-CH_3$ | 19.2 |

$^{19}$F NMR (56 MHz) analysis of the crude reaction mixture confirmed the presence of:
Iso-ester functions (R-OCOCH(CH$_3$)CF$_3$) δ −70.95 ppm (vs C$_6$F$_6$, doublet, J = 8.7 Hz)
n-esters functions (ROCOCH$_2$CH$_2$CF$_3$) δ −68.14 ppm (vs C$_6$F$_6$, triplet, J = 10.6 Hz)

Example 4—Esterification of 1234yf with Diol

The following steps were followed.
The reactor was charged with catalyst (bis(triphenylphoshine)palladium (11) chloride (2.22 g)), solvent (acetonitrile, 131.7 g) and alcohol (2,2-dimethyl propane diol, 34.9 g), inside a nitrogen purged glovebox. Then sealed and removed from the glovebox.
The reactor contents were stirred.
The HFO substrate (1234yf; 104 g) was then added from a pre-loaded and weighed sample bomb.
The reactor was then pressurised with CO to c.a. 107 berg and the reactor contents heated to the desired reaction temperature (120° C.) with stirring.
After 66 hours the pressure had dropped to 57 barg.
At the end of the experiment the reactor contents were cooled, and any residual pressure vented before the crude product was recovered.
The recovered crude product was analysed by GC-MS and NMR spectroscopy.
GC-MS analysis of the crude reaction mixture showed that the reaction mixture comprised all 5 possible ester products:

| Product | GC-MS Area % |
|---|---|
| $H_3C-\overset{CH_2OCOCF(CH_3)CF_3}{\underset{CH_2OCOCF(CH_3)CF_3}{\overset{|}{C}}}-CH_3$ | 63.7 |
| $H_3C-\overset{CH_2OCOCH_2CHFCF_3}{\underset{CH_2OCOCH_2CHFCF_3}{\overset{|}{C}}}-CH_3$ | 2.0 |
| $H_3C-\overset{CH_2OCOCH_2CHFCF_3}{\underset{CH_2OCOCF(CH_3)CF_3}{\overset{|}{C}}}-CH_3$ | 29.4 |
| $H_3C-\overset{CH_2OCOCF(CH_3)CF_3}{\underset{CH_2OH}{\overset{|}{C}}}-CH_3$ | 1.6 |
| $H_3C-\overset{CH_2OCOCH_2CHFCF_3}{\underset{CH_2OH}{\overset{|}{C}}}-CH_3$ | 3.3 |

$^{19}$F NMR (56 MHz) analysis of the crude reaction mixture confirmed the presence of:
Iso-ester functions (R-OCOCF(CH$_3$)CF$_3$) δ (vs C$_6$F$_6$): CF$_3$ −80.6 ppm, CF −169 (multiplet)
n-esters functions (ROCOCH$_2$CHFCF$_3$) δ (vs C$_6$F$_6$): CF$_3$ −80.6 ppm, CHF −201 (multiplet)

Example 5—Esterification of 1234yf with Triol

The following steps were followed.
The reactor was charged with catalyst (bis(triphenylphoshine)palladium (II) chloride (1.91 g)), solvent (acetonitrile, 130.54 g) and alcohol (1,1,1-Tris(hydroxylmethyl)propane, 29.44 g), inside a nitrogen purged glovebox. Then sealed and removed from the glovebox.
The reactor contents were stirred.
The HFO substrate (1234yf, 92 g) was then added from a pre-loaded and weighed sample bomb.
The reactor was then pressurised with CO to c.a. 107 barg and the reactor contents heated to the desired reaction temperature (120° C.) with stirring.
As the pressure dropped in the reactor it was re-pressurised to 107 barg with CO twice
After 79 hours the final pressure was 68 barg.
At the end of the experiment the reactor contents were cooled, and any residual pressure vented before the crude product was recovered.
The recovered crude product was analysed by GC-MS.
A complex mixture of esters was produced, and the yield of these esters was estimated to be 104 g.

Example 6—Esterification of a Propenyl Ether

The following steps were followed.
The reactor was charged with catalyst (bis(di(tert butyl)(4 trifluoromethyl)phenyl(phosphine) palladium chloride (0.37)), solvent (acetonitrile, 29.1 g) and alcohol (ethanol, 10.16 g) and the propenyl ether (3,3,3-trifluoro-1 (2,2,2-trifluoroethoxy)prop-1-ene (13.3 g), inside a nitrogen purged glovebox. Then sealed and removed from the glovebox.
The reactor contents were stirred.
The reactor was then pressurised with CO to c.a. 107 barg and the reactor contents heated to the desired reaction temperature (120° C.) with stirring (300 rpm).
After 90 hours the pressure had dropped by 7.2 barg.
At the end of the experiment the reactor contents were cooled, and any residual pressure vented before the crude product was recovered.
The recovered reaction mixture was analysed by $^{19}F$ NMR, which showed signals at −60.93 and −64.96 ppm corresponding to the $CF_3$ (highlighted and underlined) groups in the acyl fragments of the products. These signals were in a ratio of 1:1 with the overlapping signals centred on −75.74 of the $CF_3$ groups in the ether functional group $OCH_2CF_3$ of both of the isomeric products.

Products

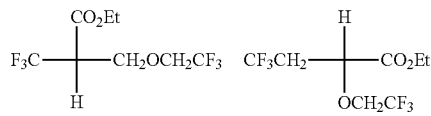

Analysis of the crude reaction mixture by GC-MS showed that (excluding solvent and excess ethanol) the crude product comprised a mixture of these esters (84.7%) and unconverted feedstock (11.4%).

FIGURES

FIG. 1 shows MS data for product of 1234ze carbonylation with ethanol $C_6H_8O_2F_4$ MW 188. In the figure the following peaks have been assigned; m/z: 187 [$M^+$−1H], 173 [$M^+$−15 ($CH_3$)], 161 [$M^+$−27 ($C_2H_3$)], 143 [$M^+$−45 ($OCH_2CH_3$)], 121 [$C_4H_3F_2O_2^+$], 115 [$M^+$−73 ($CO_2CH_2CH_3$)], 95 [$C_3F_3H_2^+$], 69 [$CF_3^+$], 51 [$CHF_2^+$], 45 [$OCH_2CH_3^+$].

FIG. 2 shows MS data for product of 1234yf carbonylation with ethanol. $C_6H_8O_2F_4$ MW 188. In the figure the following peaks have been assigned; m/z: 187 [$M^+$−1 H], 173 [$M^+$−15 ($CH_3$)], 161 [$M^+$−27 ($C_2H_3$)], 143 [$M^+$−45 ($OCH_2CH_3$)], 115 [$M^+$−73 ($CO_2CH_2CH_3$)], 96 [$C_3F_3H_3+$], 94 [$C_3F_3H^+$], 69 [$CF_3^+$], 65 [$C_2H_3F_2^+$], 51 [$CHF_2^+$], 45 [$OCH_2CH_3^+$].

Figure 1:
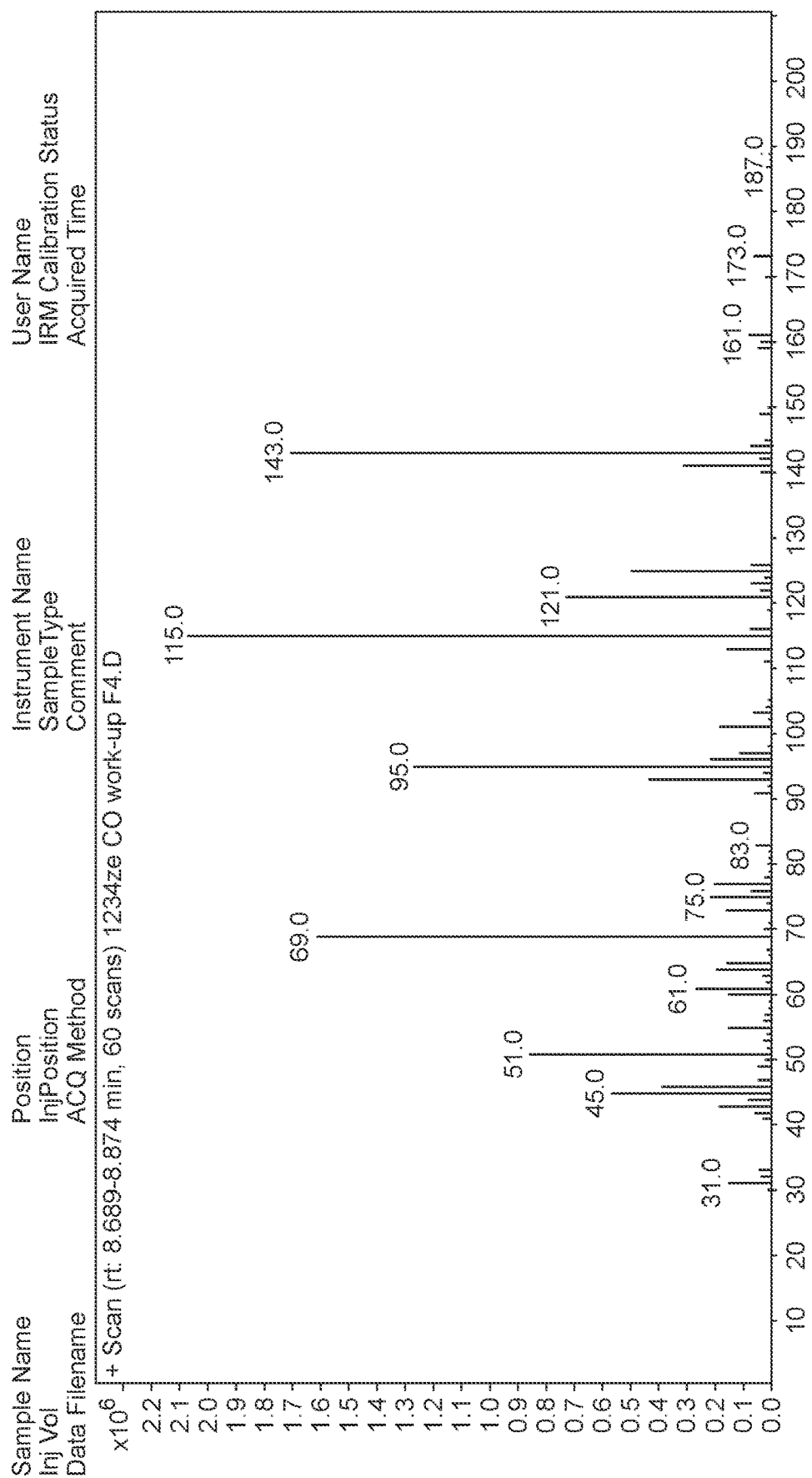
FIGS. 1-11 illustrate the results of various spectroscopic analytical techniques carried out on some of the reaction products from the Examples.
Figure 2:
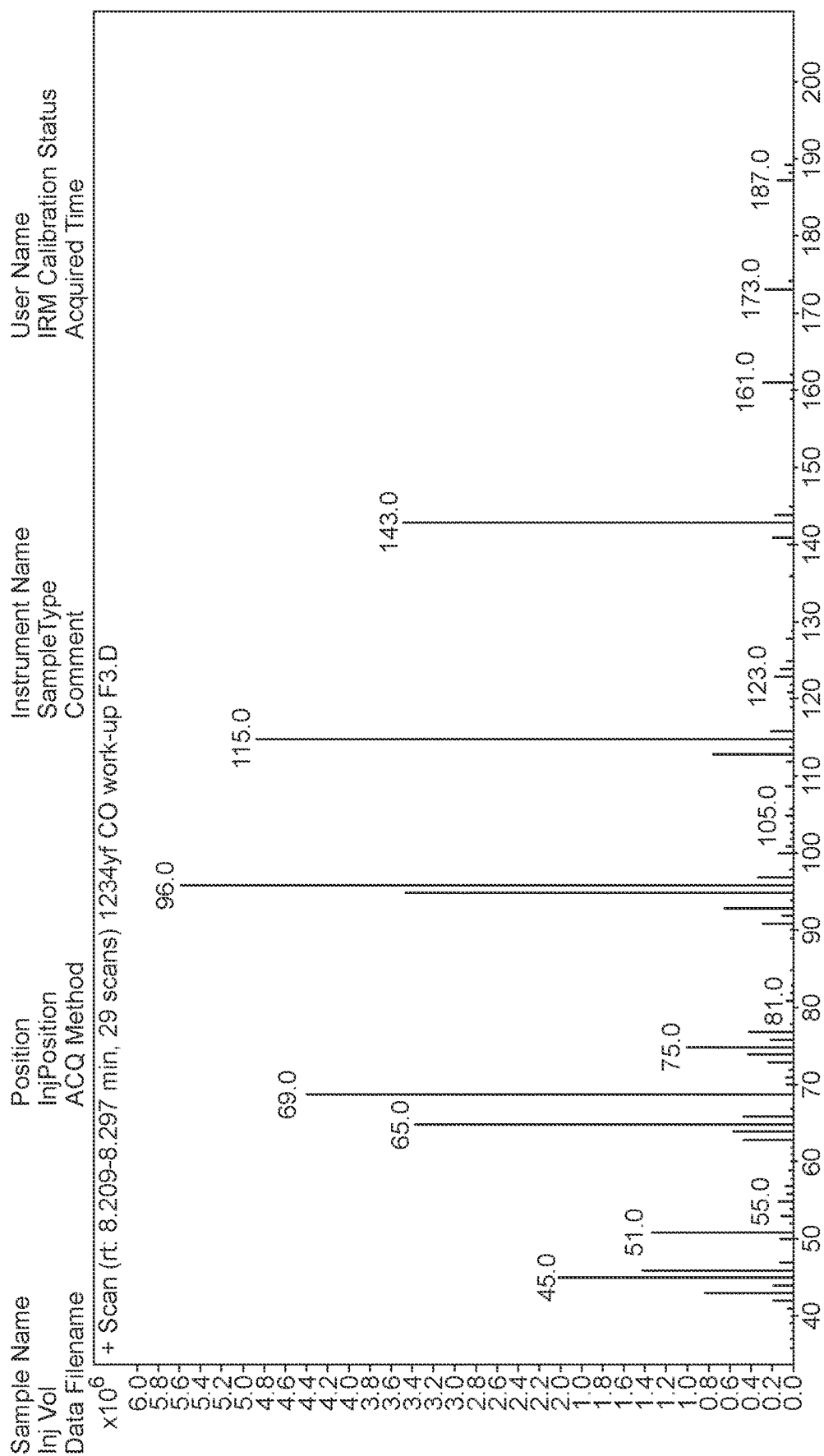
Figure 3:
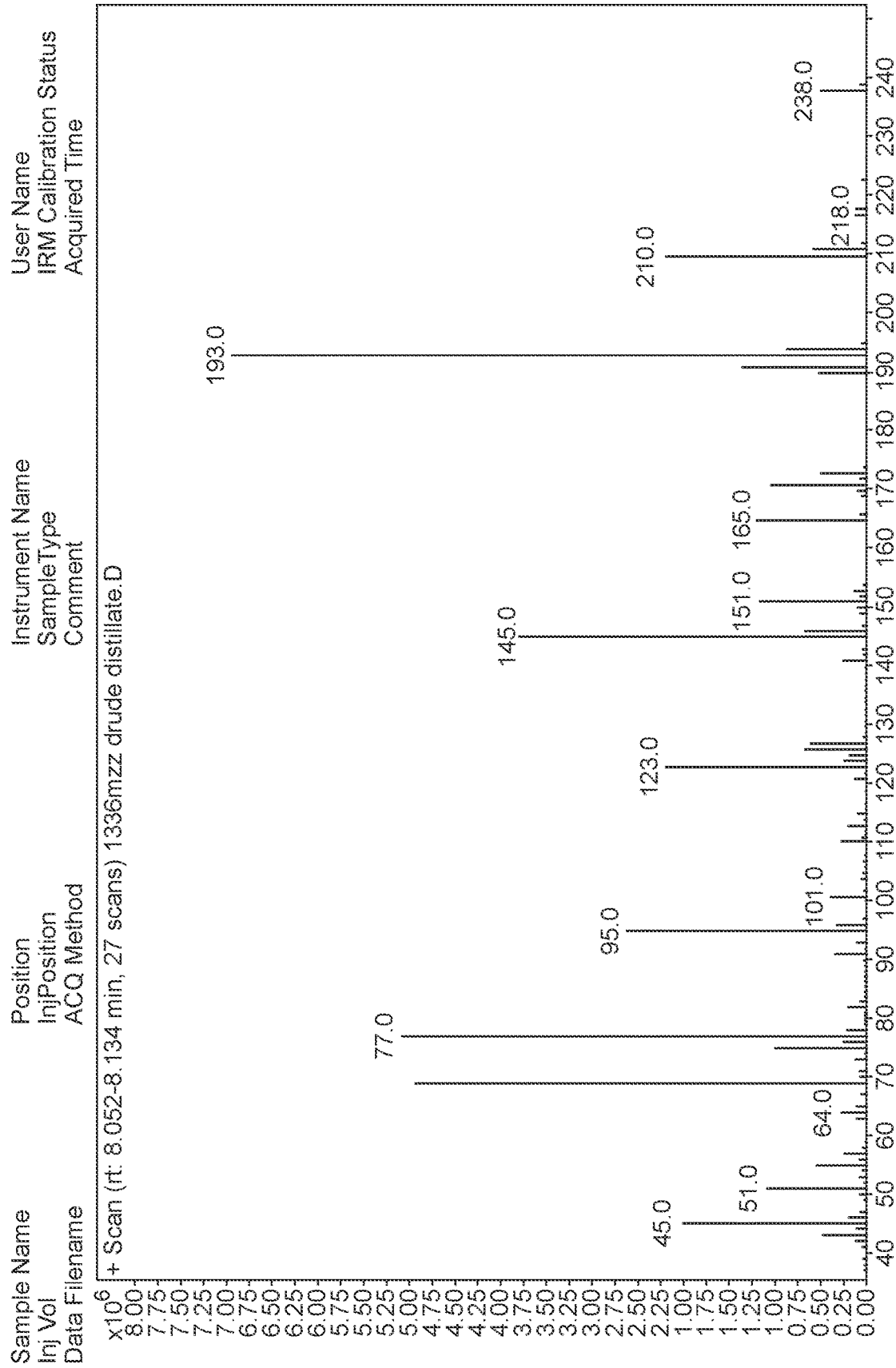

FIG. 3 shows MS data for product of 1336mzz carbonylation with ethanol. $C_7H_8O_2F_6$ MW 238. In the figure the following peaks have been assigned; m/z: 238 [$M^+$], 218 [$M^+$−20 (HF)], 210 [$M^+$−28 ($C_2H_4$)], 193 [$M^+$−45 ($OCH_2CH_3$)], 165 [$M^+$−73 ($CO_2CH_2CH_3$)], 151 [$C_3HF_6^+$], 145 [$C_4H_2F_5^+$], 123 [$C_4F_2H_5O_2^+$], 95 [$C_3F_3H_2^+$], 77[$C_3H_3F_2^+$], 69 [$CF_3^+$], 51 [$CHF_2^+$], 45 [$OCH_2CH_3+$].

Figure 4:
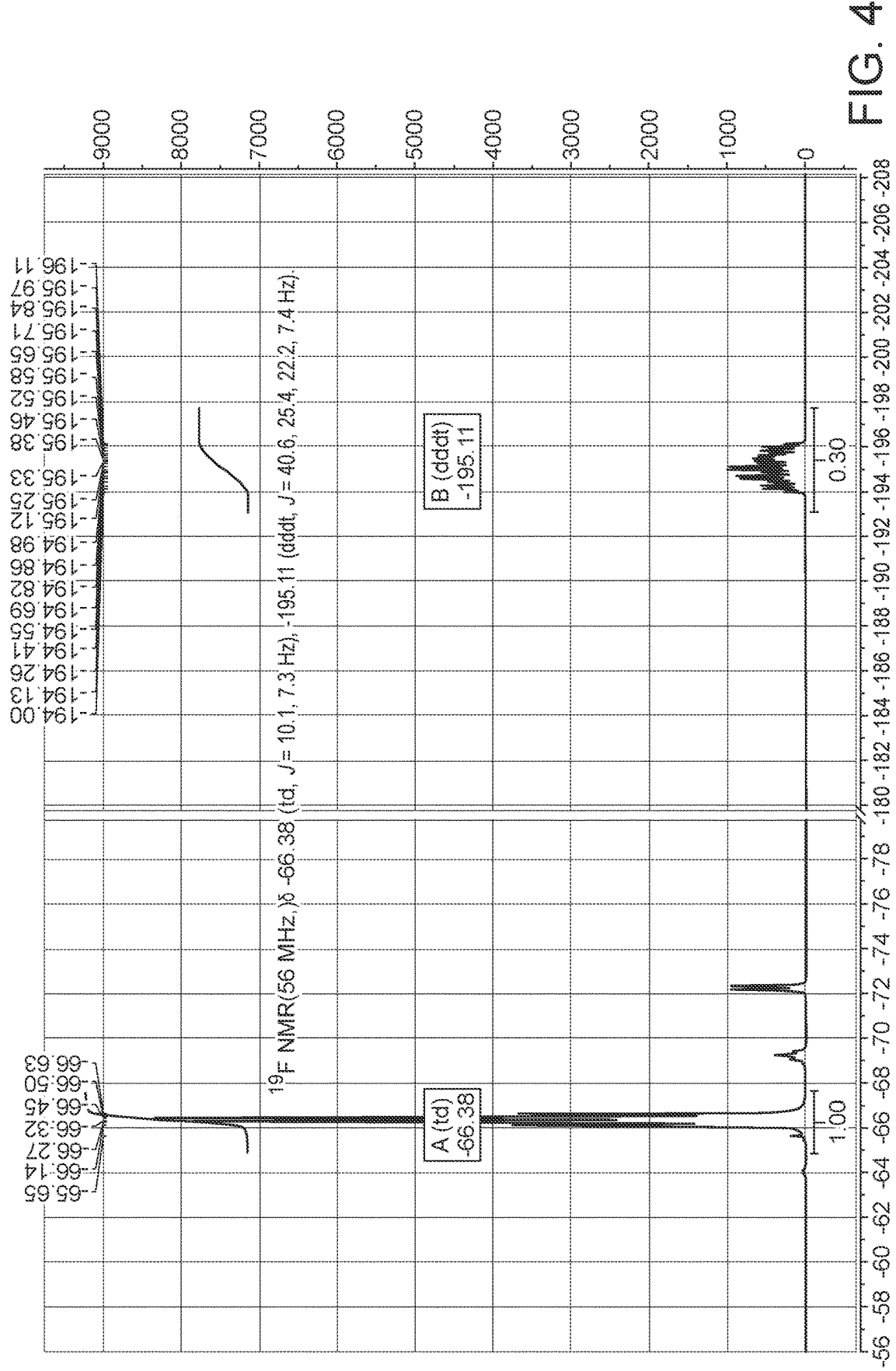

FIG. 4 shows a $^{19}F$ NMR spectrum of a 1234ze ethoxy-carbonylation reaction product.

Figure 5:
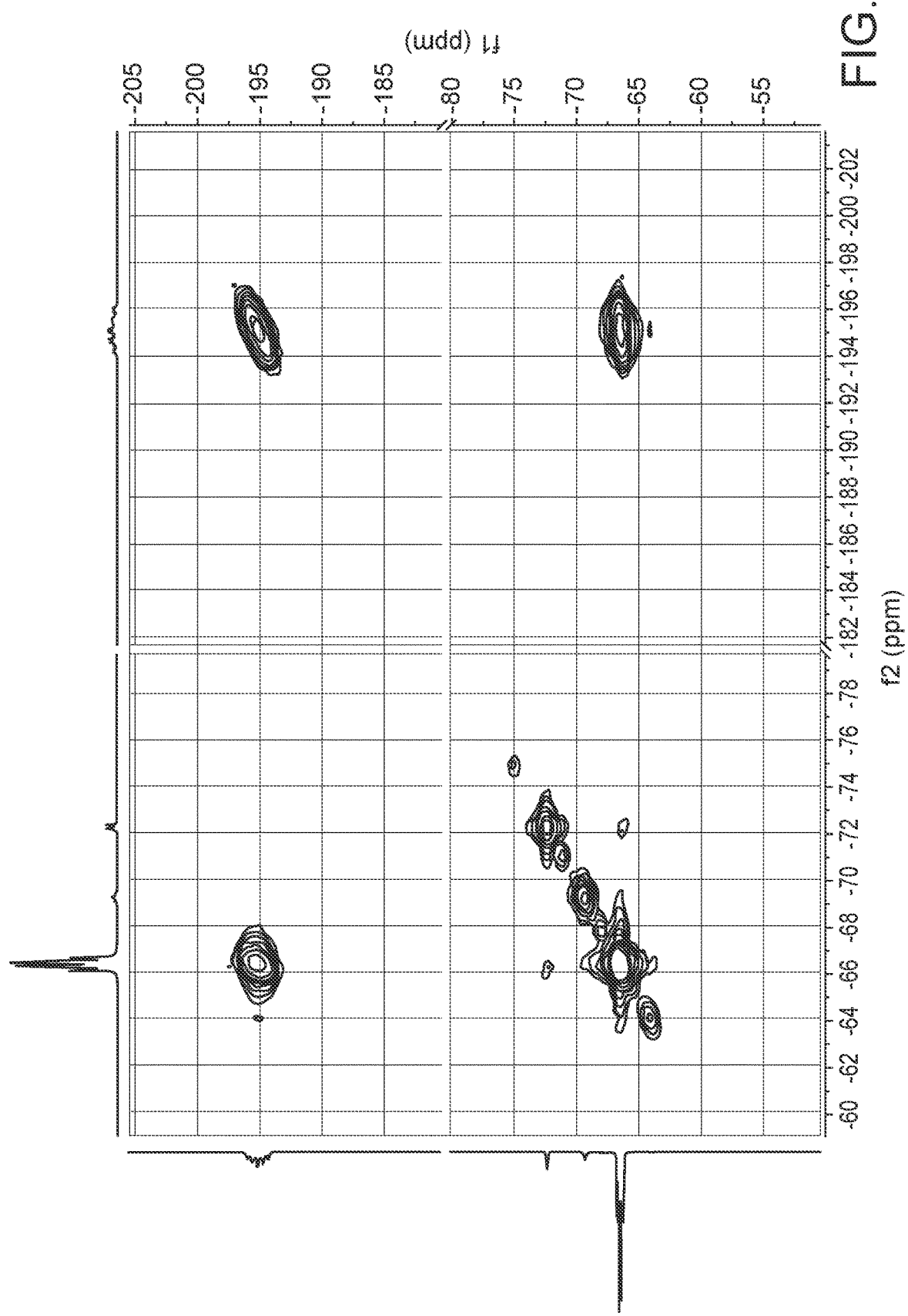

FIG. 5 shows a $^{19}F$ COSY NMR spectrum of a 1234ze ethoxy-carbonylation reaction product.

Figure 6:
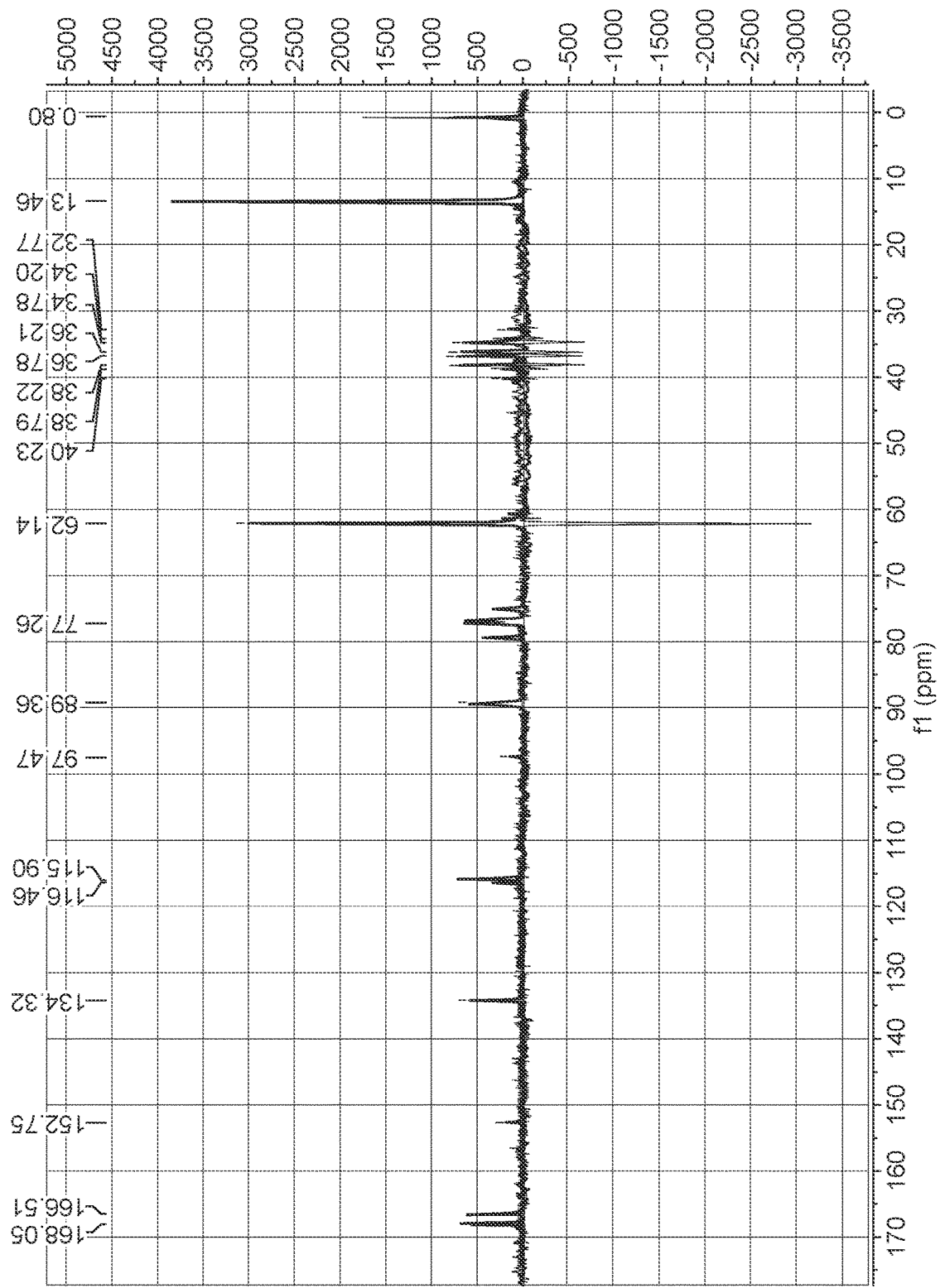

FIG. 6 shows $^{13}C$ CPD (red) and DEPT135 (blue) NMR spectra of a 1234ze ethoxy-carbonylation reaction product.

Figure 7:
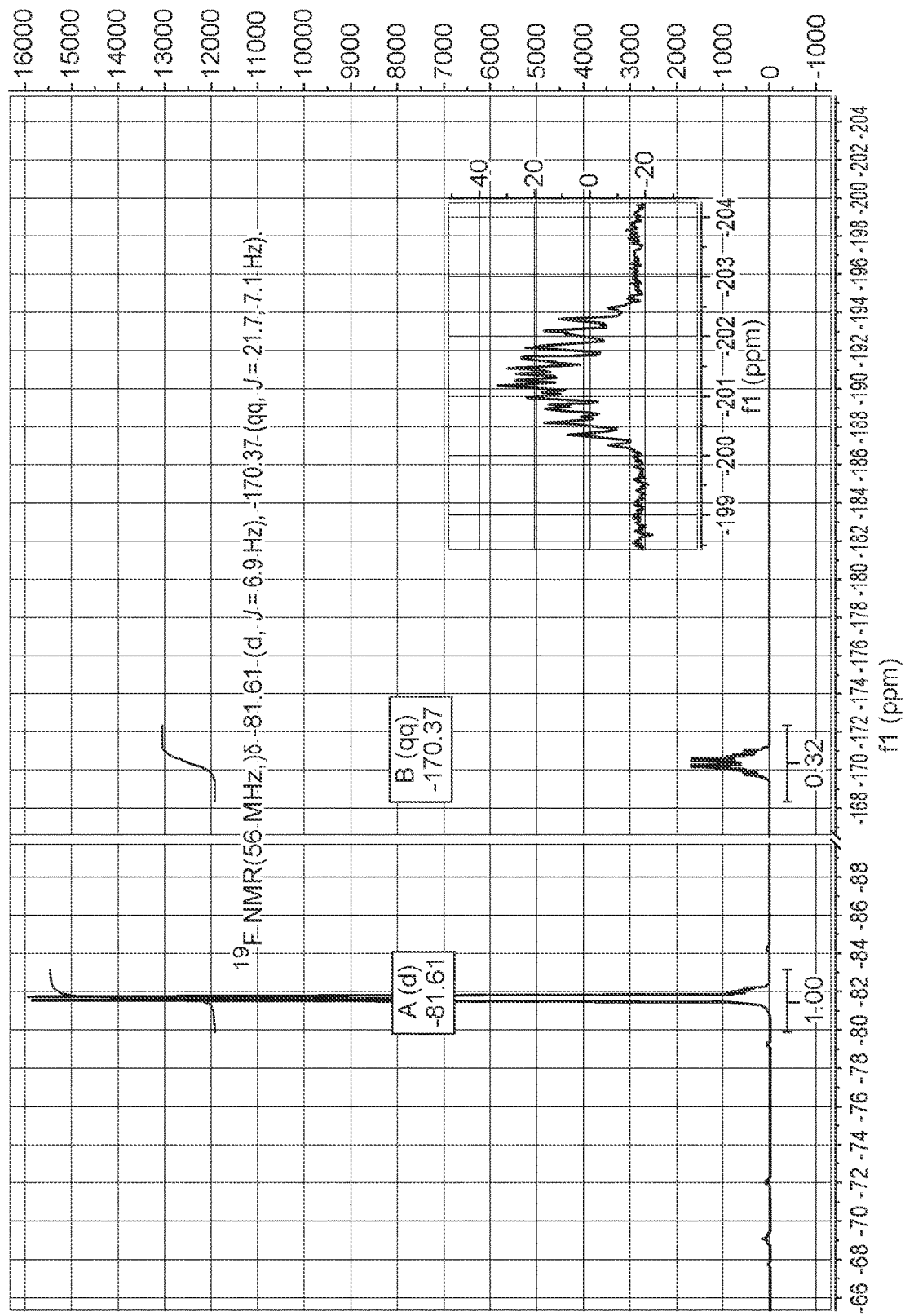

FIG. 7 shows a $^{19}F$ NMR spectrum of a 1234yf ethoxy-carbonylation reaction product.

Figure 8:
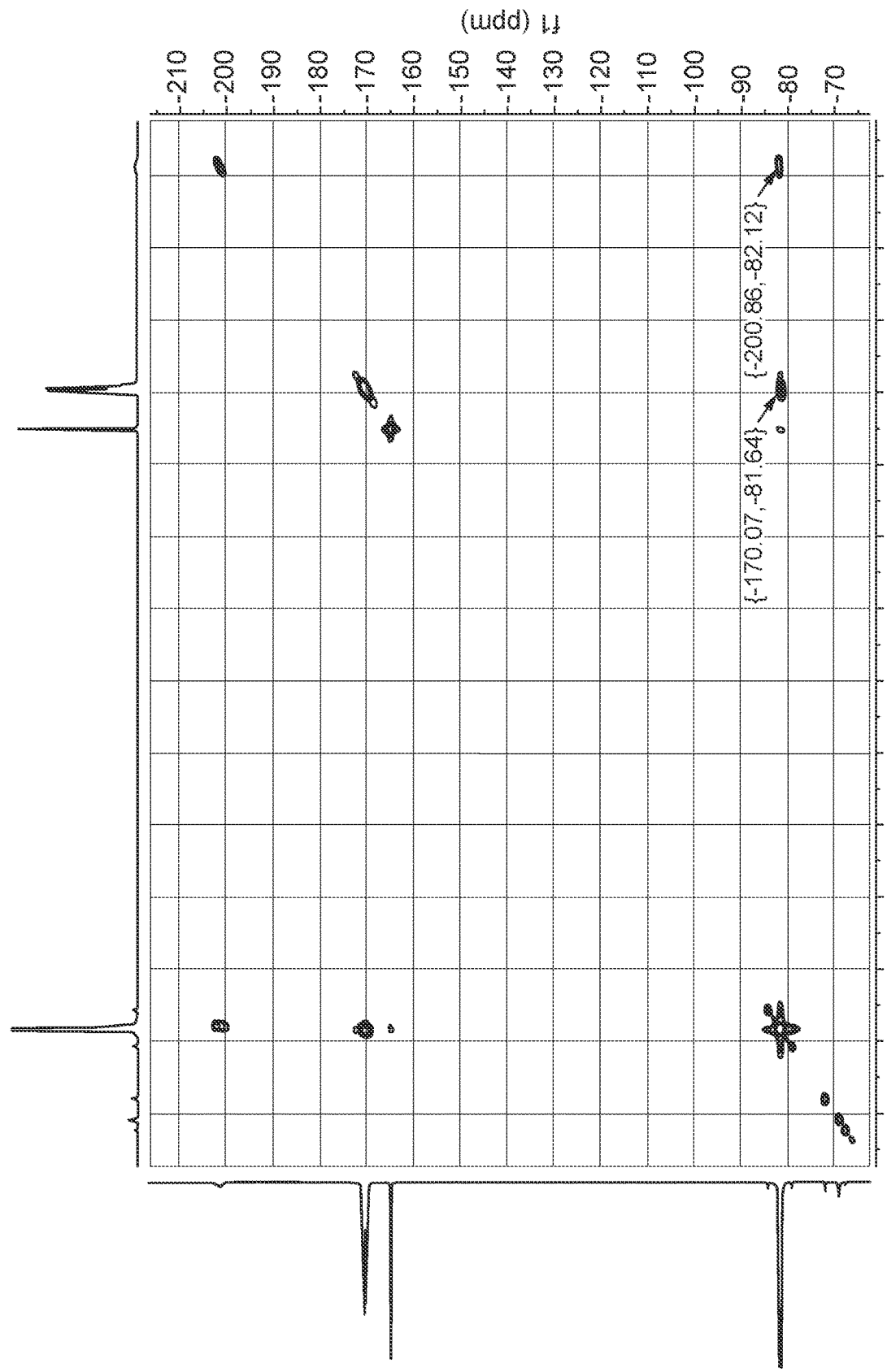

FIG. 8 shows a $^{19}F$ COSY NMR spectrum of a 1234yf ethoxy-carbonylation reaction product.

Figure 9:
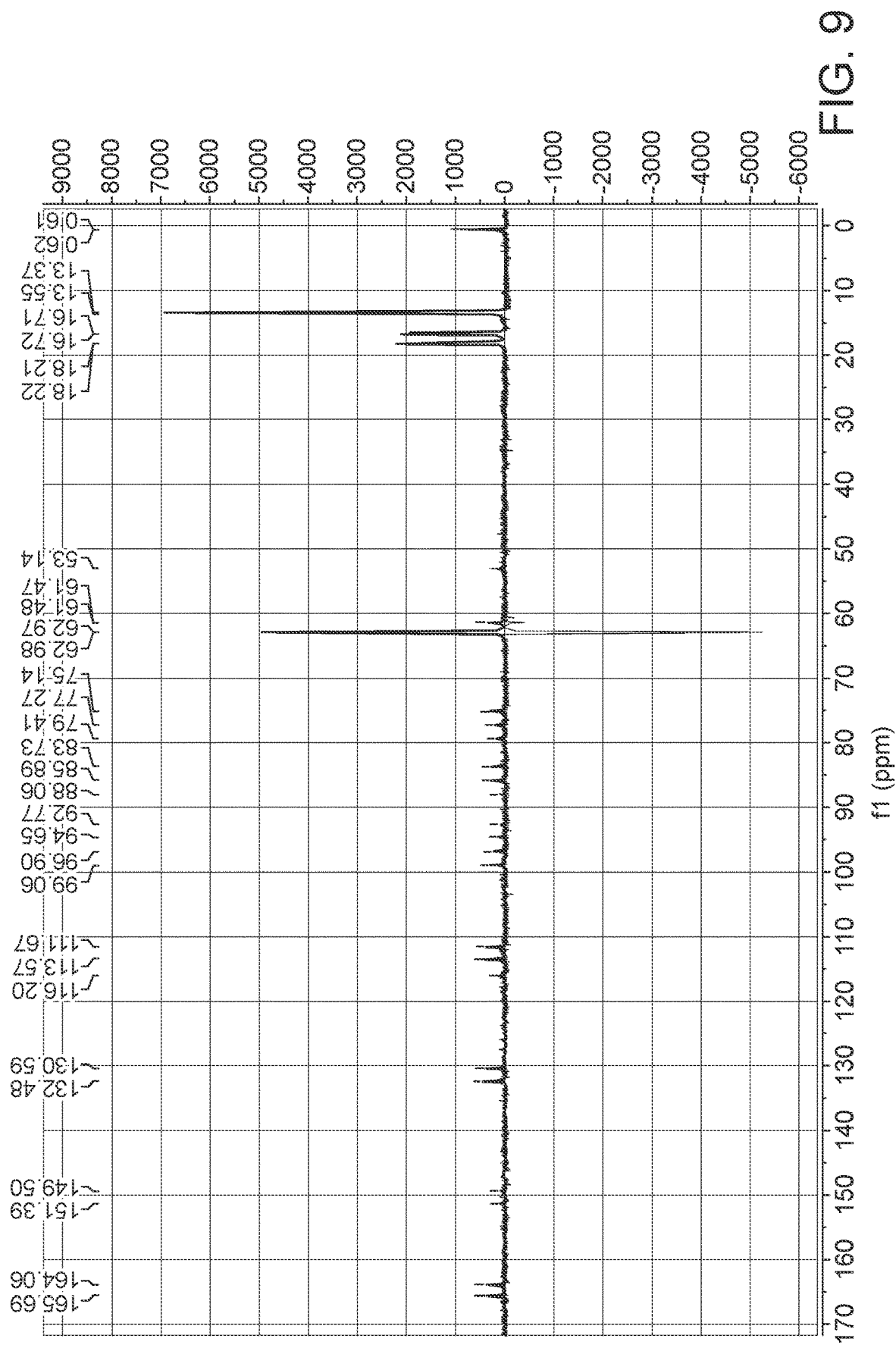

FIG. 9 shows $^{13}C$ CPD (red) and DEPT135 (blue) NMR spectra of a 1234yf ethoxy-carbonylation reaction product.

Figure 10:
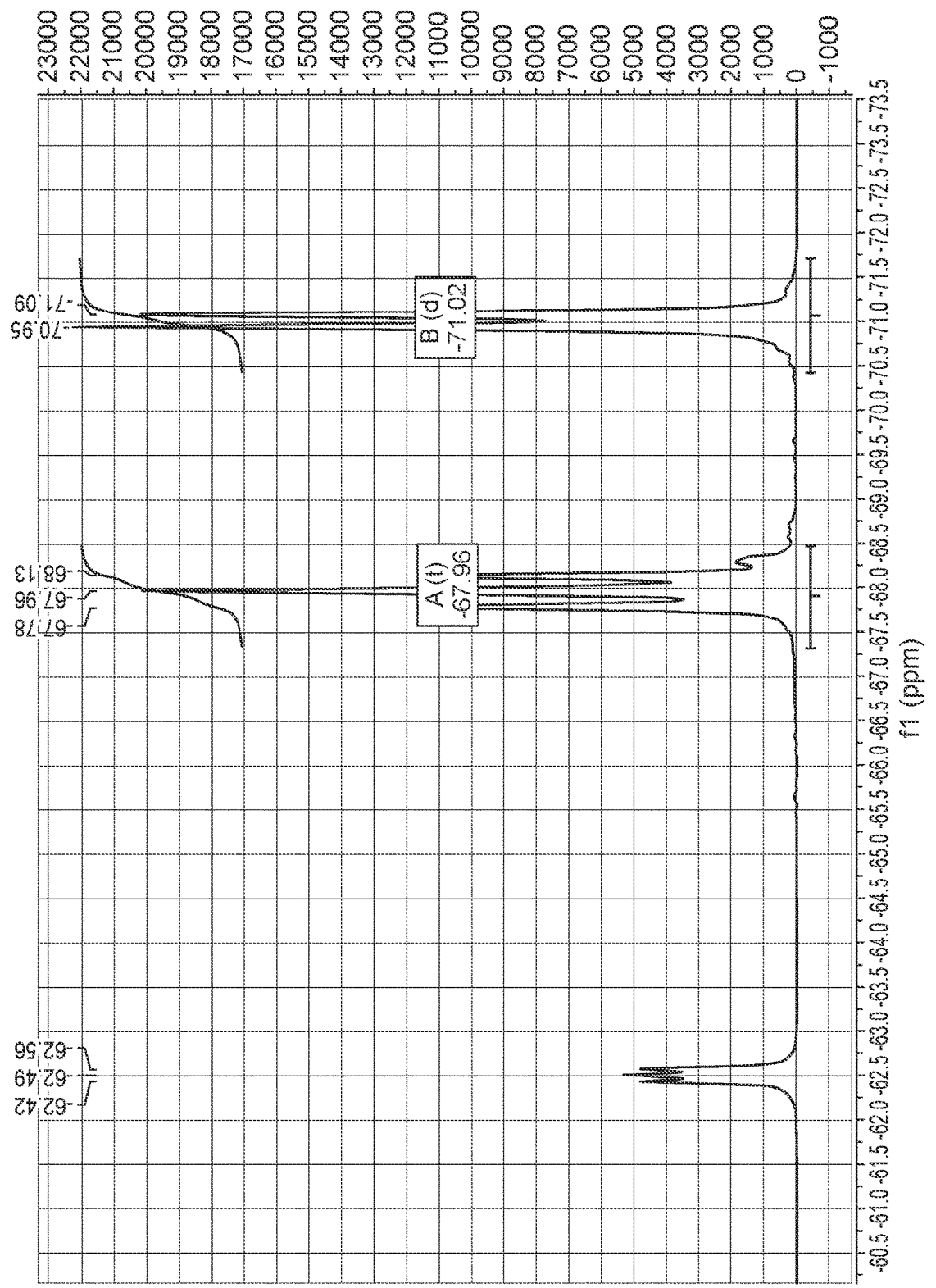

FIG. 10 shows $^{19}F$ NMR spectrum of a 1336mzz ethoxy-carbonylation reaction product.

Figure 11:
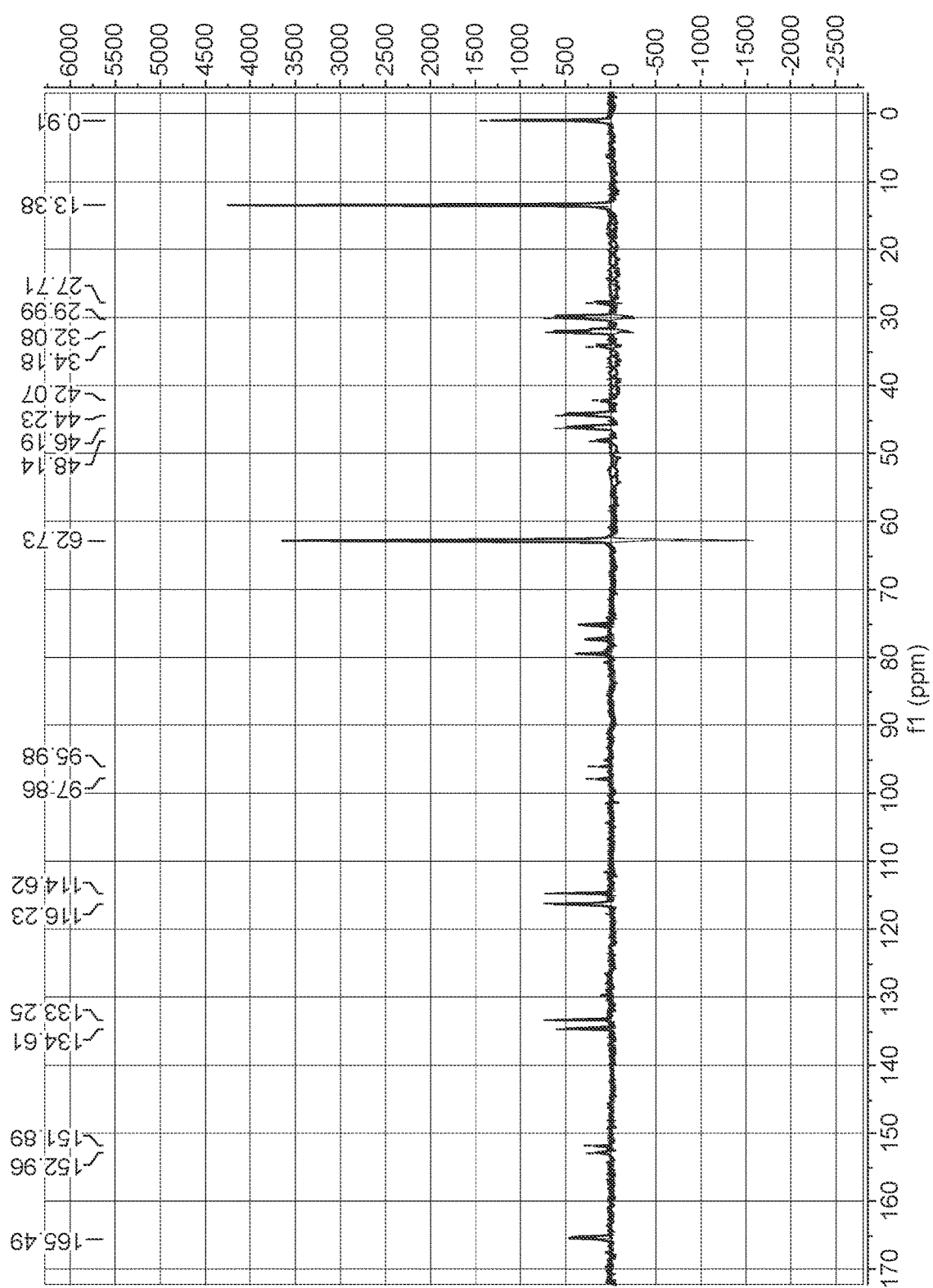

FIG. 11 shows $^{13}C$ CPD (red) and DEPT135 (blue) NMR spectra of a 1336mzz ethoxy-carbonylation reaction product.

The invention claimed is:
1. A method for preparing a partially fluorinated ester comprising acyl and alkoxy groups wherein the acyl group comprises a branched or linear fluorine containing $C_4$-$C_8$ group with one of the structures:

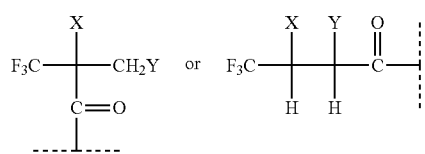

wherein X and Y are independently selected from:
H, —$CH_3$, —F, —Cl, —$CH_2F$, —$CF_3$, —$OCF_3$, —$OCH_2CF_3$, $OCH_2CF_2CHF_2$ and —$CH_2CF_3$, wherein both X and Y cannot be H, comprising (wherein both X and Y cannot be H)
comprising reacting an unsaturated halocarbon:

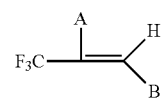

wherein A and B are independently selected from the group comprising —H, —$CH_3$, —F, —Cl, —$CH_2F$, —CF$_3$, —OCF$_3$, —OCH$_2$CF$_3$, OCH$_2$CF$_2$CHF$_2$ and —CH$_2$CF$_3$, wherein both X and Y cannot be H, with with carbon monoxide and an alcohol, in the presence of a catalyst.

2. A method according to claim 1, where the acyl group has 3 to 7 carbon atoms.

3. A method according to claim 1, wherein the acyl group comprises CF$_3$—C$_2$H$_3$FCO, CF$_3$CH$_2$CH(F)CO, CF$_3$CH(CH$_2$F)CO, CF$_3$CF(CH$_3$)CO, CF$_3$—C$_3$H$_3$F$_3$CO, or CF$_3$CH$_2$CH(CF$_3$)CO.

4. A method according to claim 1, comprising reacting 2,3,3,3-Tetrafluoropropene (1234yf) with carbon monoxide and an alcohol of formula ROH to form CF$_3$CF(CH$_3$)CO$_2$R and/or CF$_3$CHFCH$_2$CO$_2$R; or reacting 2-chloro-3,3,3-trifluoropropene (1233xf) with carbon monoxide and an alcohol to form CF$_3$CCl(CH$_3$)CO$_2$R and/or CF$_3$CHClCH$_2$CO$_2$R.

5. A method according to claim 1, comprising reacting 1,3,3,3-Tetrafluoropropene (1234ze) with carbon monoxide and an alcohol of formula ROH to form to form CF$_3$CH(CH$_2$F)CO$_2$R and/or CF$_3$CH$_2$CHFCO$_2$R.

6. A method according to claim 1, comprising reacting 1,1,1,4,4,4-hexafluoro-2-butene (1336mzz) with carbon monoxide and an alcohol of formula ROH to form CF$_3$CH$_2$CH(CF$_3$)CO$_2$R.

7. A method according to claim 1, wherein the alkoxy group is derived from a branched or linear monohydric alcohol with the formula HOC$_n$H$_{2n+1-x}$F$_x$, wherein n is from 1 to 10 and x has a value from 0 to 2n+1.

8. A method according to claim 1, wherein the catalyst comprises a group 8-12 metallic compound, and comprising a halogen ligand and a phosphorous-containing ligand or comprising a carbonyl ligand.

9. A method according to claim 8, wherein the group 8-12 metallic compound is selected from the group consisting of iron, ruthenium, osmium, cobalt rhodium, iridium, nickel, palladium, platinum, copper, silver, gold, zinc, cadmium, and mercury.

10. A method according to claim 8, wherein when the catalyst comprises the halogen ligand and the phosphorous-containing ligand, the halogen ligand is selected from the group consisting of fluorine, chlorine, bromine and iodine, and the phosphorous-containing ligand is selected from the group consisting of PH$_3$ and PPh$_3$.

11. A method according to claim 8, wherein when the catalyst comprises the carbonyl ligand, the catalyst comprises another ligand selected from the group consisting of halogen, alkyl, and phosphorous-containing compounds.

* * * * *